United States Patent
Krüger et al.

(10) Patent No.: US 11,357,574 B2
(45) Date of Patent: Jun. 14, 2022

(54) SURGICAL INSTRUMENT AND METHOD FOR DETECTING THE POSITION OF A SURGICAL INSTRUMENT

(71) Applicant: Intersect ENT International GmbH, Hennigsdorf (DE)

(72) Inventors: Timo Krüger, Berlin (DE); Dirk Mucha, Glienicke/Nordbahn (DE)

(73) Assignee: Intersect ENT International GmbH, Hennigsdorf (DE)

( * ) Notice: Subject to any disclaimer, the term of this patent is extended or adjusted under 35 U.S.C. 154(b) by 290 days.

(21) Appl. No.: 15/033,146

(22) PCT Filed: Oct. 31, 2014

(86) PCT No.: PCT/EP2014/073493
§ 371 (c)(1),
(2) Date: Apr. 29, 2016

(87) PCT Pub. No.: WO2015/063280
PCT Pub. Date: May 7, 2015

(65) Prior Publication Data
US 2016/0249986 A1    Sep. 1, 2016

(30) Foreign Application Priority Data
Oct. 31, 2013    (DE) .................... 10 2013 222 230.0

(51) Int. Cl.
*A61B 34/20*    (2016.01)
*A61B 90/98*    (2016.01)
(Continued)

(52) U.S. Cl.
CPC .............. *A61B 34/20* (2016.02); *A61B 90/98* (2016.02); *A61B 2017/0046* (2013.01);
(Continued)

(58) Field of Classification Search
CPC .. A61B 2034/2046–2065; A61B 34/20; A61B 2034/2068–2072; A61B 17/00234–2017/00353
See application file for complete search history.

(56) References Cited

U.S. PATENT DOCUMENTS

| 4,905,698 A |   | 3/1990 | Strohl |
|---|---|---|---|
| 5,554,155 A | * | 9/1996 | Awh .................... A61F 9/00736 604/20 |

(Continued)

FOREIGN PATENT DOCUMENTS

| CN | 101084840 A | 12/2007 |
|---|---|---|
| CN | 102056544 A | 5/2011 |

(Continued)

OTHER PUBLICATIONS

International Search Report dated Jan. 20, 2015, for PCT Application No. PCT/EP2014/073493, filed on Oct. 31, 2014, 3 pages.

(Continued)

*Primary Examiner* — Tan-Uyen T Ho
*Assistant Examiner* — Charles M Wei
(74) *Attorney, Agent, or Firm* — Cooley LLP (57) ABSTRACT

The invention relates to a surgical instrument with an instrument handle, an instrument shank connected to the instrument handle, an instrument tip with a work point, which instrument tip is connected to the instrument shank, and a first locator arranged on the instrument handle or the instrument shank. During a use of the surgical instrument, the instrument shank can be deflected, e.g. on account of transverse forces, at least between the first locator and the work point. A second locator is arranged at a distance from the first locator and, by comparison with the latter, closer to the work point, wherein the second locator is designed to detect five degrees of freedom.

17 Claims, 5 Drawing Sheets

(51) Int. Cl.
  *A61B 17/00* (2006.01)
  *A61B 90/00* (2016.01)
(52) U.S. Cl.
  CPC ............ *A61B 2034/2051* (2016.02); *A61B 2034/2055* (2016.02); *A61B 2034/2063* (2016.02); *A61B 2034/2072* (2016.02); *A61B 2090/3983* (2016.02)

(56) References Cited

U.S. PATENT DOCUMENTS

| | | | |
|---|---|---|---|
| 5,586,989 A * | 12/1996 | Bray, Jr. | ........ A61B 17/320708 606/160 |
| 5,840,024 A | 11/1998 | Taniguchi | |
| 5,944,023 A | 8/1999 | Johnson | |
| 5,964,759 A * | 10/1999 | Yamanashi | ............ A61B 18/12 606/50 |
| 5,971,997 A | 10/1999 | Guthrie | |
| 6,011,987 A | 1/2000 | Barnett | |
| 6,052,610 A | 4/2000 | Koch | |
| 6,161,032 A | 12/2000 | Acker | |
| 6,235,038 B1 | 5/2001 | Hunter | |
| 6,248,074 B1 | 6/2001 | Ohno | |
| 6,301,495 B1 | 10/2001 | Gueziec | |
| 6,370,420 B1 | 4/2002 | Kraft | |
| 6,432,041 B1 | 8/2002 | Taniguchi | |
| 6,611,141 B1 * | 8/2003 | Schulz | ................. G01C 21/165 324/207.12 |
| 6,618,612 B1 | 9/2003 | Acker | |
| 6,661,571 B1 | 12/2003 | Shioda | |
| 6,690,960 B2 | 2/2004 | Chen | |
| 7,043,961 B2 | 5/2006 | Pandey | |
| 7,346,417 B2 | 3/2008 | Lüth | |
| 7,474,327 B2 | 1/2009 | Davidson | |
| 7,491,198 B2 | 2/2009 | Kockro | |
| 8,067,726 B2 | 11/2011 | Groszmann | |
| 8,207,863 B2 | 6/2012 | Neubauer | |
| 9,208,561 B2 | 12/2015 | Kruger | |
| 9,333,047 B2 | 5/2016 | Mucha | |
| 9,410,802 B2 | 8/2016 | Mucha | |
| 9,471,850 B2 | 10/2016 | Kruger | |
| 9,641,808 B2 | 5/2017 | Rose | |
| 10,362,966 B2 | 7/2019 | Kruger | |
| 10,368,851 B2 | 8/2019 | Tuma | |
| 10,398,512 B2 | 9/2019 | Mucha | |
| 10,512,522 B2 | 12/2019 | Verard | |
| 10,568,713 B2 | 2/2020 | Kruger | |
| 11,065,061 B2 | 7/2021 | Makower | |
| 11,109,915 B2 | 9/2021 | Mucha | |
| 11,123,144 B2 | 9/2021 | Bustan | |
| 2001/0021806 A1 | 9/2001 | Gueziec | |
| 2003/0040670 A1 * | 2/2003 | Govari | ................... A61B 5/015 600/424 |
| 2003/0059097 A1 | 3/2003 | Abovitz | |
| 2003/0066538 A1 | 4/2003 | Maartinelli | |
| 2003/0069588 A1 * | 4/2003 | Vilsmeier | ............. A61B 90/36 606/116 |
| 2003/0209096 A1 | 11/2003 | Pandey | |
| 2003/0229279 A1 | 12/2003 | Amstutz | |
| 2003/0231793 A1 | 12/2003 | Crampton | |
| 2004/0019274 A1 | 1/2004 | Galloway, Jr. et al. | |
| 2004/0024309 A1 | 2/2004 | Ferre | |
| 2004/0054489 A1 | 3/2004 | Moctezuma De La Barrera | |
| 2004/0073279 A1 | 4/2004 | Malackowski | |
| 2004/0143183 A1 | 7/2004 | Toyoda | |
| 2004/0169673 A1 | 9/2004 | Crampe | |
| 2004/0199072 A1 | 10/2004 | Sprouse | |
| 2004/0230199 A1 | 11/2004 | Jansen | |
| 2004/0263535 A1 | 12/2004 | Birkenbach | |
| 2005/0020909 A1 | 1/2005 | Moctezuma de la Barrera | |
| 2005/0024043 A1 | 2/2005 | Govari | |
| 2005/0054895 A1 | 3/2005 | Hoeg | |
| 2005/0085717 A1 | 4/2005 | Shahidi | |
| 2005/0085720 A1 * | 4/2005 | Jascob | ..................... A61B 5/06 600/424 |
| 2005/0101966 A1 | 5/2005 | Lavallee | |
| 2005/0107687 A1 | 5/2005 | Anderson | |
| 2005/0119639 A1 | 6/2005 | McCombs | |
| 2005/0149050 A1 | 7/2005 | Stifter | |
| 2005/0187562 A1 | 8/2005 | Grimm | |
| 2005/0215854 A1 | 9/2005 | Ozaki | |
| 2005/0228270 A1 | 10/2005 | Lloyd | |
| 2005/0228274 A1 | 10/2005 | Boese | |
| 2005/0288576 A1 | 12/2005 | Febert | |
| 2006/0033679 A1 | 2/2006 | Gunji | |
| 2006/0058604 A1 | 3/2006 | Avinash | |
| 2006/0100526 A1 | 5/2006 | Yamamoto | |
| 2006/0122497 A1 | 6/2006 | Glossop | |
| 2006/0161059 A1 | 7/2006 | Wilson | |
| 2006/0211914 A1 | 9/2006 | Hassler | |
| 2006/0241397 A1 | 10/2006 | Govari | |
| 2006/0264749 A1 | 11/2006 | Weiner | |
| 2006/0271056 A1 | 11/2006 | Terill-Grisoni | |
| 2007/0034731 A1 | 2/2007 | Falco | |
| 2007/0070194 A1 | 3/2007 | Abe | |
| 2007/0106114 A1 | 5/2007 | Sugimoto | |
| 2007/0111726 A1 | 5/2007 | Lambert | |
| 2007/0135803 A1 | 6/2007 | Belson | |
| 2007/0167754 A1 | 7/2007 | Okuno | |
| 2007/0182729 A1 | 8/2007 | Klingenbeck-regn | |
| 2007/0197896 A1 | 8/2007 | Moll | |
| 2007/0287905 A1 | 12/2007 | Klingenbeck-Regn | |
| 2008/0009697 A1 | 1/2008 | Haider | |
| 2008/0021317 A1 | 1/2008 | Sumanaweera | |
| 2008/0071142 A1 | 3/2008 | Gattani | |
| 2008/0077158 A1 | 3/2008 | Haider | |
| 2008/0103509 A1 | 5/2008 | Goldbach | |
| 2008/0132932 A1 * | 6/2008 | Hoeppner | ...... A61B 17/320016 606/184 |
| 2008/0139916 A1 | 6/2008 | Maier | |
| 2008/0162074 A1 | 7/2008 | Schneider | |
| 2008/0204000 A1 | 8/2008 | Groszmann | |
| 2008/0218588 A1 | 9/2008 | Stetten | |
| 2008/0221442 A1 | 9/2008 | Tolkowsky | |
| 2008/0228188 A1 | 9/2008 | Birkbeck | |
| 2008/0228195 A1 * | 9/2008 | von Jako | ........... A61B 19/5244 606/130 |
| 2008/0255442 A1 | 10/2008 | Ashby et al. | |
| 2008/0262345 A1 | 10/2008 | Fichtinger | |
| 2008/0275334 A1 | 11/2008 | Berting | |
| 2008/0287802 A1 | 11/2008 | Li | |
| 2008/0294034 A1 | 11/2008 | Krueger | |
| 2008/0319448 A1 | 12/2008 | Lavallee et al. | |
| 2009/0030428 A1 * | 1/2009 | Omori | .................... A61B 34/70 606/130 |
| 2009/0068620 A1 | 3/2009 | Knobel | |
| 2009/0069671 A1 | 3/2009 | Anderson | |
| 2009/0192519 A1 | 7/2009 | Omori | |
| 2009/0228813 A1 | 9/2009 | Sekiguchi | |
| 2009/0234329 A1 | 9/2009 | Inamoto | |
| 2009/0306499 A1 | 12/2009 | Van Vorhis | |
| 2010/0019918 A1 | 1/2010 | Avital | |
| 2010/0121174 A1 | 5/2010 | Osadchy et al. | |
| 2010/0137707 A1 | 6/2010 | Hunter | |
| 2010/0160771 A1 | 6/2010 | Gielen | |
| 2010/0210939 A1 | 8/2010 | Hartmann | |
| 2010/0220914 A1 | 9/2010 | Iwase | |
| 2010/0228117 A1 | 9/2010 | Hartmann | |
| 2010/0229118 A1 | 9/2010 | Dorn | |
| 2010/0234724 A1 | 9/2010 | Jacobson | |
| 2010/0249506 A1 | 9/2010 | Prisco | |
| 2010/0307516 A1 | 12/2010 | Neubauer et al. | |
| 2010/0312247 A1 | 12/2010 | Tuma | |
| 2011/0015523 A1 | 1/2011 | Sabata | |
| 2011/0054449 A1 | 3/2011 | Tien | |
| 2011/0060213 A1 | 3/2011 | Mire | |
| 2011/0066029 A1 | 3/2011 | Lyu | |
| 2011/0118557 A1 | 5/2011 | McKenna | |
| 2011/0137156 A1 | 6/2011 | Razzaque | |
| 2011/0178389 A1 | 7/2011 | Kumar | |
| 2011/0270083 A1 | 11/2011 | Shen | |
| 2011/0288600 A1 | 11/2011 | Ritchey | |
| 2011/0295329 A1 | 12/2011 | Fitz | |

(56) References Cited

U.S. PATENT DOCUMENTS

| | | | |
|---|---|---|---|
| 2011/0313414 A1* | 12/2011 | Liu | A61B 5/6852 606/41 |
| 2012/0007747 A1 | 1/2012 | Boike | |
| 2012/0136626 A1* | 5/2012 | Mucha | A61B 34/20 702/150 |
| 2012/0143050 A1 | 6/2012 | Heigl | |
| 2012/0157887 A1 | 6/2012 | Fanson | |
| 2012/0165655 A1* | 6/2012 | Mucha | A61B 34/30 600/420 |
| 2012/0168587 A1 | 7/2012 | Karsak | |
| 2012/0188352 A1 | 7/2012 | Wittenberg | |
| 2013/0023730 A1 | 1/2013 | Kitamura | |
| 2013/0060146 A1 | 3/2013 | Yang | |
| 2013/0060278 A1 | 3/2013 | Bozung | |
| 2013/0211763 A1 | 8/2013 | Mucha | |
| 2013/0258079 A1 | 10/2013 | Rose | |
| 2014/0005555 A1 | 1/2014 | Tesar | |
| 2014/0051922 A1 | 4/2014 | Guthart | |
| 2014/0148808 A1 | 5/2014 | Inkpen | |
| 2014/0200621 A1 | 7/2014 | Malackowski | |
| 2014/0275987 A1 | 9/2014 | Bzostek | |
| 2014/0303489 A1 | 10/2014 | Meier | |
| 2014/0314297 A1 | 10/2014 | Krueger | |
| 2014/0317910 A1 | 10/2014 | Govari | |
| 2015/0087968 A1 | 3/2015 | Kruger | |
| 2015/0170366 A1 | 6/2015 | Kruger | |
| 2015/0182297 A1 | 7/2015 | Sandhu | |
| 2016/0100899 A1* | 4/2016 | Jinno | A61B 34/30 606/130 |
| 2016/0106338 A1 | 4/2016 | Kruger | |
| 2016/0143700 A1 | 5/2016 | Kruger | |
| 2016/0175543 A1* | 6/2016 | Frankhouser | A61B 17/3476 606/130 |
| 2016/0213430 A1 | 7/2016 | Mucha | |
| 2016/0249986 A1 | 9/2016 | Kruger | |
| 2016/0310041 A1 | 10/2016 | Jenkins | |
| 2016/0331269 A1 | 11/2016 | Kruger | |
| 2017/0105809 A1 | 4/2017 | Kruger | |
| 2017/0196508 A1 | 7/2017 | Hunter | |
| 2017/0258526 A1 | 9/2017 | Lang | |
| 2017/0270678 A1 | 9/2017 | Masumoto | |
| 2018/0021092 A2 | 1/2018 | Tausch | |
| 2019/0015644 A1 | 1/2019 | Thompson | |
| 2019/0038366 A1 | 2/2019 | Johnson | |
| 2019/0099141 A1 | 4/2019 | Garlow | |

FOREIGN PATENT DOCUMENTS

| | | |
|---|---|---|
| CN | 102917647 A | 2/2013 |
| DE | 19641720 | 4/1998 |
| DE | 19944981 A1 | 4/2001 |
| DE | 202 20 584 U1 | 4/2004 |
| DE | 10 2004 058272 | 6/2005 |
| DE | 69732362 T2 | 3/2006 |
| DE | 10 2004 017834 | 5/2007 |
| DE | 10 2006 052 886 A1 | 5/2007 |
| DE | 2020 07004507 U1 | 6/2007 |
| DE | 10 2006 003 610 A1 | 8/2007 |
| DE | 10 2007 059691 A1 | 7/2008 |
| DE | 10 2008 057744 A1 | 5/2010 |
| DE | 10 2009 030731 A1 | 12/2010 |
| DE | 10 2010 027535 A1 | 1/2012 |
| DE | 102010027535 A1 | 1/2012 |
| DE | 10 2011 119 073 A1 | 5/2013 |
| EP | 0691663 A1 | 1/1996 |
| EP | 1278458 B1 | 1/2003 |
| EP | 1380266 A1 | 1/2004 |
| EP | 1523951 A2 | 4/2005 |
| EP | 1080695 A1 | 5/2005 |
| EP | 1900336 A1 | 3/2008 |
| EP | 1 915 962 A1 | 4/2008 |
| EP | 1925265 B1 | 1/2010 |
| EP | 2179703 A1 | 4/2010 |
| EP | 2186474 A1 | 5/2010 |
| EP | 2305115 A1 | 4/2011 |
| EP | 2305115 A1 | 11/2011 |
| EP | 3506278 A1 | 7/2019 |
| JP | 2004-529679 | 9/2004 |
| JP | 2011-036600 | 2/2011 |
| WO | WO 1996/05768 A1 | 2/1996 |
| WO | WO 1997/29678 A2 | 8/1997 |
| WO | WO 1999/32033 A1 | 7/1999 |
| WO | WO 2002/076302 A2 | 10/2002 |
| WO | WO 2005/039391 A2 | 5/2005 |
| WO | WO 2006/095027 A1 | 9/2006 |
| WO | WO 2006/122001 A2 | 11/2006 |
| WO | WO 2007/011314 A2 | 1/2007 |
| WO | WO 2007/017642 A1 | 2/2007 |
| WO | WO 2007/115825 A1 | 10/2007 |
| WO | WO 2008/030263 A1 | 3/2008 |
| WO | WO 2008/076079 A1 | 6/2008 |
| WO | WO 2008/095068 A1 | 8/2008 |
| WO | WO 2008/110553 A2 | 9/2008 |
| WO | WO 2009/150564 A3 | 12/2009 |
| WO | WO 2010/054645 A2 | 5/2010 |
| WO | WO 2010/054646 A3 | 5/2010 |
| WO | WO 2010/076676 A1 | 7/2010 |
| WO | WO 2010/123858 A2 | 10/2010 |
| WO | WO 2010/133320 A1 | 11/2010 |
| WO | WO 2011/081690 A1 | 7/2011 |
| WO | WO 2011/134083 A1 | 11/2011 |
| WO | WO 2011/148299 A1 | 12/2011 |
| WO | WO 2012/056034 A1 | 5/2012 |
| WO | WO 2012/109760 A1 | 8/2012 |
| WO | 2012/150567 A1 | 11/2012 |
| WO | WO 2012/150567 A1 | 11/2012 |
| WO | WO 2013/010138 A2 | 1/2013 |
| WO | WO 2013/013718 A1 | 1/2013 |
| WO | WO-2013/072434 A1 | 5/2013 |
| WO | 2013/109527 A1 | 7/2013 |
| WO | WO 2013/109527 A1 | 7/2013 |
| WO | WO 2013/144334 A1 | 10/2013 |
| WO | WO 2014/184382 A1 | 11/2014 |
| WO | WO 2015/085011 A1 | 6/2015 |
| WO | WO 2017/100180 A1 | 6/2017 |
| WO | WO 2021/048439 A1 | 3/2021 |

OTHER PUBLICATIONS

Written Opinion of the International Searching Authority dated Jan. 20, 2015, for PCT Application No. PCT/EP2014/073493, filed on Oct. 31, 2014, 9 pages.

Anonymous, Inertial navigation system, Mar. 8, 2019, Retrieved from the Internet: https://en.wikipedia.org/w/index.php?title=inertial_navigation_system&oldid=886755750 XP055599140 [retrieved on Jun. 25, 2019].

BrainLab AG, Curve Dual Navigation Station—Technical User Guide Revision 1.1, Dec. 31, 2017.

Retrieved from the Internet: https://userguides.brainlab.com/wp-content/uploads/2019/12/Curve-1.2-Technical-User-Guide-English-60915-69EN-Rev.1.1.pdf.

Dang, et al., Robust methods for automatic image-to-world registration in cone-beam CT interventional guidance, Medical Physics, Oct. 2012, pp. 6484-6498, vol. 39, No. 10.

European Patent Office, International Search Report and Written Opinion for PCT/EP2011/069065, dated Dec. 23, 2011, 8 pages.

European Patent Office, International Search Report dated Jan. 20, 2015, for PCT Application No. PCT/EP2014/073493, filed on Oct. 31, 2014, 12 pages.

European Patent Office, International Search Report and Written Opinion for PCT/EP2020/059643, dated May 12, 2020, 14 pages.

European Patent Office, International Search Report and Written Opinion for International (PCT) Patent Application No. PCT/EP2012/072783, dated Feb. 13, 2013, 10 paqes.

Jing et al., Navigating System for Endoscopic Sinus Surgery Based on Augmented Reality, IEEE/ICME International Conference on Complex Medical Engineering, 2007, pp. 185-188.

Konishi et al., Augmented reality navigation system for endoscopic surgery based on three-dimensional ultrasound and computed tomography: Application to 20 clinical cases, International Congress Series 1281, 2005, pp. 537-542.

(56) References Cited

OTHER PUBLICATIONS

Maurer et al., Registration Of Head Volume Images Using Implantable Fiducial Markers, IEEE Transactions on Medical Imaging, 1997, pp. 447-462.
Maintz et al.; A Survey of Medical Image Registration, Medical Image Analysis, Jan. 1, 1998, 37 pages.
Mucha et al., Plausibility check for error compensation in electromagnetic navigation in endoscopic sinus surgery, Int. J. of Computer Assisted Radiology and Surgery (CARS), 2006, pp. 316-318.
Olwal, et al., Hybridsurface: Multi-user, multi-device, remote collaboration; Vimeo; https://vimeo.com/30581634; 2009; screen shots of video at five second intervals; entire video, 2 pages.
Olwal, et al., Design and Evaluation of Interaction Technology for Medical Team Meetings, Interact 2011, Part 1, FIP International Federation for Information Processing, 2011, pp. 505-522.
Pflugi, et al., Augmented marker tracking for peri-acetabular osteotomy surgery, 2017 39th Annual Int. Conference of the IEEE Engineering in Medicae and Biology Society (EMB), Jul. 11, 2017, pp. 937-941.
Lee et al., A Simple and Accurate Camera-Sensor Calibration for Surgical Endoscopes and Microscopes, International Conference on Computer Analysis of Images and Patterns, CAIP 2017, [Lecture Notes in Computer Science], Sep. 14, 2014, pp. 98-107.
Tsai et al., A new Technique for fully Autonomous and Efficent 3D Robots Hand/Eye Calibration, IEEE Transactions on Robotics and Automation, Jun. 1, 1989, pp. 345-358, vol. 5, No. 3.
United States Patent and Trademark Office, Non-Final Office Action for U.S. Appl. No. 14/387,722, filed Aug. 25, 2017, 11 pages.
United States Patent and Trademark Office, Non-Final Office Action for U.S. Appl. No. 14/387,722, filed Apr. 13, 2018, 22 pages.
United States Patent and Trademark Office, Final Office Action for U.S. Appl. No. 14/387,722, filed Dec. 28, 2018, 26 pages.
United States Patent and Trademark Office, Non-Final Office Action for U.S. Appl. No. 14/387,722, filed May 23, 2019, 24 pages.
United States Patent and Trademark Office, Final Office Action for U.S. Appl. No. 14/387,722, filed Dec. 31, 2019, 23 pages.
United States Patent and Trademark Office, Final Office Action for U.S. Appl. No. 14/387,722, filed Jun. 30, 2021, 27 pages.
United States Patent and Trademark Office, Non-Final Office Action for U.S. Appl. No. 14/903,381, filed Dec. 28, 2017, 18 pages.
United States Patent and Trademark Office, Final Office Action for U.S. Appl. No. 14/903,381, filed Jun. 20, 2018, 19 pages.
United States Patent and Trademark Office, Non-Final Office Action for U.S. Appl. No. 14/903,381, filed Feb. 7, 2019, 21 pages.
United States Patent and Trademark Office, Final Office Action for U.S. Appl. No. 14/903,381, filed Jul. 3, 2019, 20 pages.
United States Patent and Trademark Office, Non-Final Office Action for U.S. Appl. No. 14/903,381, filed Jan. 8, 2020, 17 pages.
United States Patent and Trademark Office, Final Office Action for U.S. Appl. No. 14/903,381, filed Jun. 23, 2020, 17 pages.
United States Patent and Trademark Office, Non-Final Office Action for U.S. Appl. No. 14/903,381, filed Nov. 24, 2020, 17 pages.
United States Patent and Trademark Office, Final Office Action for U.S. Appl. No. 14/903,381, filed May 5, 2021, 21 pages.
United States Patent and Trademark Office, Non-Final Office Action for U.S. Appl. No. 15/033,146, filed Aug. 27, 2018, 16 pages.
United States Patent and Trademark Office, Final Office Action for U.S. Appl. No. 15/033,146, filed Mar. 7, 2019, 12 pages.
United States Patent and Trademark Office, Non-Final Office Action for U.S. Appl. No. 15/033,146, filed Sep. 19, 2019, 15 pages.
United States Patent and Trademark Office, Final Office Action for U.S. Appl. No. 15/033,146, filed Apr. 16, 2020, 14 pages.
United States Patent and Trademark Office, Non-Final Office Action for U.S. Appl. No. 15/033,146, filed Sep. 30, 2020, 13 pages.
United States Patent and Trademark Office, Final Office Action for U.S. Appl. No. 15/033,146, filed Jul. 28, 2021, 21 pages.
United States Patent and Trademark Office, Final Office Action for U.S. Appl. No. 17/492,057, filed Dec. 9, 2021, 14 pages.
United States Patent and Trademark Office, Non-Final Office Action for U.S. Appl. No. 13/881,770, filed Jun. 18, 2015, 18 pages.
United States Patent and Trademark Office, Final Office Action for U.S. Appl. No. 13/881,770, filed Nov. 20, 2015, 20 pages.
United States Patent and Trademark Office, Notice of Allowance for U.S. Appl. No. 13/881,770, filed Jan. 20, 2017, 8 pages.
United States Patent and Trademark Office, Notice of Allowance for U.S. Appl. No. 14/401,652, filed Sep. 1, 2015, 13 pages.
United States Patent and Trademark Office, Non-Final Office Action for U.S. Appl. No. 14/890,480, filed Jan. 27, 2017, 20 pages.
United States Patent and Trademark Office, Final Office Action for U.S. Appl. No. 14/890,480, filed Aug. 4, 2017, 21 pages.
United States Patent and Trademark Office, Non-Final Office Action for U.S. Appl. No. 14/890,480, filed Mar. 8, 2018, 20 pages.
United States Patent and Trademark Office, Final Office Action for U.S. Appl. No. 14/890,480, filed Aug. 30, 2018, 22 pages.
United States Patent and Trademark Office, Notice of Allowance for U.S. Appl. No. 14/890,480, filed Apr. 9, 2019, 8 pages.
United States Patent and Trademark Office, Non-Final Office Action for U.S. Appl. No. 15/303,793, filed Apr. 23, 2018, 31 pages.
United States Patent and Trademark Office, Final Office Action for U.S. Appl. No. 15/303,793, filed Nov. 16, 2018, 33 pages.
United States Patent and Trademark Office, Non-Final Office Action for U.S. Appl. No. 15/303,793, filed Jun. 13, 2019, 52 pages.
United States Patent and Trademark Office, Notice of Allowance for U.S. Appl. No. 15/303,793, filed Oct. 18, 2019, 8 pages.
United States Patent and Trademark Office, Non-Final Office Action for U.S. Appl. No. 14/358,108, filed Jun. 12, 2015, 10 pages.
United States Patent and Trademark Office, Final Office Action for U.S. Appl. No. 14/358,108, filed Jan. 29, 2016, 12 pages.
United States Patent and Trademark Office, Notice of Allowance for U.S. Appl. No. 14/358,108, filed Jun. 15, 2016, 8 pages.
United States Patent and Trademark Office, Non-Final Office Action for U.S. Appl. No. 13/321,087, filed Apr. 22, 2015, 11 pages.
United States Patent and Trademark Office, Final Office Action for U.S. Appl. No. 13/321,087, filed Oct. 21, 2015, 12 pages.
United States Patent and Trademark Office, Non-Final Office Action for U.S. Appl. No. 13/321,087, filed Dec. 9, 2016, 20 pages.
United States Patent and Trademark Office, Final Office Action for U.S. Appl. No. 13/321,087, filed Sep. 21, 2017, 18 pages.
United States Patent and Trademark Office, Non-Final Office Action for U.S. Appl. No. 13/321,087, filed Jul. 13, 2018, 24 pages.
United States Patent and Trademark Office, Notice of Allowance for U.S. Appl. No. 13/321,087, filed Apr. 26, 2019, 5 pages.
United States Patent and Trademark Office, Non-Final Office Action for U.S. Appl. No. 13/380,695, filed Dec. 4, 2013, 9 pages.
United States Patent and Trademark Office, Final Office Action for U.S. Appl. No. 13/380,695, filed Jul. 16, 2014, 11 pages.
United States Patent and Trademark Office, Non-Final Office Action for U.S. Appl. No. 13/380,695, filed Dec. 9, 2014, 6 pages.
United States Patent and Trademark Office, Final Office Action for U.S. Appl. No. 13/380,695, filed Jul. 29, 2015, 5 pages.
United States Patent and Trademark Office, Notice of Allowance for U.S. Appl. No. 13/380,695, filed Feb. 17, 2016, 8 pages.
United States Patent and Trademark Office, Non-Final Office Action for U.S. Appl. No. 13/810,666, filed Dec. 18, 2015, 8 pages.
United States Patent and Trademark Office, Notice of Allowance for U.S. Appl. No. 13/810,666, filed Apr. 8, 2016, 5 pages.
Anonymous, Change System/Upgrade order 1110000092: Overview, Mar. 14, 2008, 1 page.
Anonymous, Configuration ZSY 11100000864: Result, Sep. 25, 2008, 1 page.
Anonymous, Configuration ZSY 11100000864: Result, Aug. 14, 2008, 1 page.
Anonymous, Endoscopic view of the brain, Figure 3, no date given, 1 page.
Bockholt, et al., Augmented Reality for Enhancement of Endoscopic Interventions, Proceedings of the IEEE Virtual Reality, 2003, 5 pages.
BrainLab AG, Acceptance Protocol IGS, Purchase order No. 4500239188, Dec. 11, 2008, 1 page.
BrainLab AG, Bod de Livraison, Aug. 5, 2008, 2 pages.
BrainLab AG, Clinical User Guide, VectorVision cranial/ENT, Version 7.8, 2008, 594 pages.

(56) References Cited

OTHER PUBLICATIONS

BrainLab AG, Curve Dual Navigation Station—Technical User Guide Revision 1.1, Dec. 31, 2017 Retrieved from the Internet: https://userguides.brainlab.com/wp-content/uploads/2019/12/Curve-1.2-Technical-User-Guide-English-60915-69EN-Rev.1.1.pdf.
BrainLab AG, Lieferschein, Sep. 22, 2008, 2 pages.
Dang, et al., Robust methods for automatic image-to-world registration in cone-beam CT interventional guidance; Medical Physics, AIP; vol. 39, No. 10; Oct. 2012; pp. 6484-6498.
Devernay, et al., 3D Reconstruction of the Operating Field for Image Overlay in 3D-Endoscopic Surgery, Nov. 2001, 1 page.
Devernay, Toward Endoscopic Augmented Reality for Robotically Assisted Minimally Invasive Cardiac Surgery, Feb. 2001, 6 pages.
European Patent Office, International Search Report and Written Opinion for PCT/EP2013/056802, dated Jul. 12, 2013, 12 pages.
European Patent Office, International Search Report and Written Opinion for PCT/EP2014/072282, dated Jan. 27, 2015, 12 pages.
European Patent Office, International Search Report and Written Opinion for PCT/EP2010/003822, dated Sep. 10, 2010, 13 pages.
European Patent Office, International Search Report and Written Opinion for PCT/EP2015/058107, dated Oct. 22, 2015, 10 pages.
European Patent Office, International Search Report and Written Opinion for PCT/EP2010/002991, dated Sep. 6, 2010, 11 pages.
European Patent Office, International Search Report and Written Opinion for PCT/EP2014/068447, dated Feb. 5, 2015, 14 pages.
European Patent Office, International Search Report and Written Opinion for PCT/EP2011/003563, dated Nov. 14, 2014, 12 pages.
European Patent Office, International Search Report and Written Opinion for PCT/EP2014/065030, dated Oct. 8, 2014, 12 pages.
European Patent Office, International Search Report and Written Opinion for PCT/EP2020/062086, dated Aug. 7, 2020, 10 pages.
European Patent Office, International Search Report and Written Opinion for International (PCT) Patent Application No. PCT/EP2012/072783, dated Feb. 13, 2013, 10 pages.
European Patent Office, European Extended Search Report for EP 19169312.6, dated Jul. 3, 2019, 12 pages.
Fleig, et al., Surface Reconstruction of the Surgical Field from Stereoscopic Microscope Views in Neurosurgery, International Congress Series 1230, 2001, pp. 268-274.
Hirai, et al., Image-Guided Neurosurgery System Integrating AR-Based Navigation and Open-MRI monitoring, Computer Aided Surgery, Mar. 2005, pp. 59-71, vol. 10, No. 2.
Jain, Fundamentals of Digital Image Processing, Prentice-Hall Inc., 1989, 4 pages.
Lapeer, et al., Image-enhanced Surgical Navigation for Endoscopic Sinus Surgery: Evaluating Calibration, Registration and Tracking, The International Journal of Medica Robotics and Computer Assisted Surgery, 2008, pp. 32-45, No. 4.
Mourgues, et al., 3D Reconstruction of the Operating Field for Image Overlay in 3D-Endoscopic Surgery, Proceedings IEEE and ACM International Symposium on Augmented Reality, Oct. 29-30, 2001, 1 page.
Paul, et al., Augmented Virtuality Based on Stereoscopic Reconstruction in Multimodal Image-Guided Neurosurgery: Methods and Performance Evaluation, Methods and Performance Evaluation, IEEE Transactions on Medical Imaging, 2005, pp. 1500-1511, vol. 24.
Rogalla, et al., Virtual Endoscopy and Related 3D Techniques, Medical Radiology Diagnostic Imaging, 2001, 8 pages.
Sielhorst, et al., Advanced Medical Displays: A Literature Review of Augmented Realityjournal of Display Technology, Dec. 2008, pp. 451-467, vol. 4, No. 4.
Thormahlen, Professor of Philips-Universitat Marburg biography, retrieved on Oct. 8, 2019, 9 pages.
Thormahlen, Three-Dimensional Endoscopy, Kluwer Academic Publishers, Dec. 2002, pp. 199-214.
United States Patent and Trademark Office, Non-Final Office Action for U.S. Appl. No. 15/033,146, filed Mar. 10, 2022, 6 pages.
United States Patent and Trademark Office, Final Office Action for U.S. Appl. No. 17/492,057, filed Mar. 9, 2022, 8 pages.
Von F. Hagenmuller, et al., Medical Imaging in Gastroenterology and Hepatology (Falk Symposium, Band 124), Dec. 2002, 3 pages.
Von F. Hagenmuller, et al., Medical Imaging in Gastroenterology and Hepatology (Falk Symposium, Band 124), [Book Description], 2 pages.
Von F. Hagenmuller, et al., Medical Imaging in Gastroenterology and Hepatology, Kluwer Academic Publishers, 2002, 3 pages.

* cited by examiner

SURGICAL INSTRUMENT AND METHOD FOR DETECTING THE POSITION OF A SURGICAL INSTRUMENT

CROSS REFERENCE TO RELATED APPLICATIONS

This application is the U.S. National Stage of International Application Number PCT/EP2014/073493 filed on Oct. 31, 2014 which application claims priority under 35 USC § 119 to German Patent Application No. 10 2013 222 230.0 filed on Oct. 31, 2013. Both applications are hereby incorporated by reference in their entirety.

TECHNICAL FIELD

The invention relates to a surgical instrument with a locator arrangement for improved determination of the position of the instrument tip in a position detection system. The invention also relates to a method for detecting the position of a surgical instrument.

BACKGROUND OF THE INVENTION

A position detection system is a system for determining position data—namely the location and orientation—of the work point of a medical instrument, such as e.g. a sickle knife, antrum spoon, pointer, scalpel, electrotome or cautery knife, within a reference coordinate system. The work point of a medical instrument is, for example, the distal end of an instrument tip. A reference coordinate system is a coordinate system of a position detection apparatus or position detection system. With the aid of the position information and data about the form and dimension of the medical instrument, the medical instrument can be displayed, true to its position in the reference coordinate system, on a display unit. With the aid of the position detection system, the image, true to its position, of the medical instrument is displayable in a superimposed manner on an image, true to its position, of the respective body part of the patient.

For the purposes of planning and carrying out invasive surgical interventions, it is common practice to use image data, obtained preoperatively, of an operation region or intervention region in the interior of the patient, such as x-ray recordings, sonography recordings, computed tomography (CT) recordings or magnetic resonance imaging (MRI) recordings, as planning data. The intervention region is the region in and on the body of the patient in which the operative measure, such as e.g. the severing of a tissue part, the closure of a vessel or the insertion of an implant, is carried out during the operative intervention, while the operating region is the entire region on and in the body of the patient which is affected during the operative intervention, for example also by merely guiding along surgical instruments.

Moreover, it is usual to display, next to one another or in a superimposed fashion, image data obtained intraoperatively, e.g. endoscopic live video or CT recordings, and image data obtained preoperatively on a display unit such as a monitor. In this way, e.g. tissue to be removed, such as tumors, and sensitive objects, such as nerve (pathways), muscles, tendons, organs or vessels, which lie in the operating region and which are potentially at risk by the operative intervention can be highlighted graphically and therefore made more visible to the surgeon. In this way, the position detection system assists the surgeon in using the medical devices used during the operation in the most efficient manner possible and with as little impairment as possible of the surrounding tissue of the patient. Since the position detection system already transforms the position data of the medical device into the reference coordinate system, a corresponding step is dispensed with for the surgeon, and so he can substantially concentrate on the individual steps of the operation to be carried out. As a result of this, it is possible to significantly reduce both the duration of the operation and the health risk to the patient generated by the operation.

When carrying out an operation, the medical instrument must initially be navigated as exactly as possible along a predetermined path into the intervention region, usually set preoperatively, in the body of the patient so as not to damage adjacent tissue. In so doing, the surgeon can substantially concentrate on the superimposed illustration of the surgical instrument with the image data of the operating region of the patient, and on the guidance of the surgical instrument. In the intervention region, the surgeon carries out the operative measure as precisely as possible in order, firstly, to achieve the operation goal, e.g. complete removal of a predetermined tissue part or complete closure of a vessel, and, secondly, to damage as little of the surrounding healthy tissue as possible. After completing the operative measure, the medical instrument must be guided out of the intervention region and out of the operating region again in a controlled and precise fashion along a predetermined path.

To this end, a plurality of different location detection or position detection systems, which assist in navigating medical instruments, such as e.g. surgical instruments, in the operating region in and on the body of the patient, are known. These systems detect the coordinate transform between the patient and at least one medical instrument e.g. continuously or intermittently during the operation. Furthermore, position detection systems, by means of which the position of a multiplicity of different medical instruments is detectable and transferable into the reference coordinate system, are known. The established position data are generally displayed on a display unit, together with the planning data obtained preoperatively and/or the image data obtained intraoperatively.

So that position detection systems are able to detect the position of medical instruments and the patient, use is made of locators which are attached to the medical instruments and the patient. Locators are usually already integrated in the corresponding medical instruments, while the patient locator, e.g. in the form of a headband, still needs to be fastened to the patient prior to the operation. Initially, the positions of the individual locators in the reference coordinate system of the position detection system are determinable with the aid of the locators.

A locator can detect a certain number of degrees of freedom. Six degrees of freedom need be established for a complete determination of the position of a three-dimensional object, such as e.g. a surgical instrument, in a three-dimensional space with Cartesian axes X, Y, Z, namely three translational ones (X'-, Y'-, Z'-component) and three rotational ones (rotation about the X'-, Y'-, Z'-axis). There are locators which are embodied to detect all six degrees of freedom. By way of example, other locators can only detect five or fewer degrees of freedom. Accordingly, it is not possible to uniquely determine the position of an object using a locator embodied to detect fewer than six degrees of freedom. Instead, it is possible to combine a plurality of locators in order to detect all degrees of freedom required for a unique position determination together.

Moreover, there are different types of locators, such as e.g. optical, acoustic or electromagnetic locators.

Optical locators have reflectors or optical marker points, the image of which should be identifiable as easily and as unambiguously as possible in a recording. The images of the optical locators can be evaluated in a photogrammetric fashion by an evaluation unit in order thus to determine the position of the optical locator in the reference coordinate system. Instead of dedicated optical locators, there can also be optical position detection on the basis of a characteristic form of the respective instrument. Slightly more evaluation outlay may then possibly be required. Within the meaning thereof, characteristic forms of an instrument can also form a locator for determining all six degrees of freedom by means of an optical position detection system. Optical position detection systems are advantageous in that they hardly emit electromagnetic interference fields and do not produce measurement errors, even in the case of strong electromagnetic interference fields. It is disadvantageous that optical locators have a larger build relative to electromagnetic locators and only work if no obstacles are arranged between the light source or reception unit and the locator.

Electromagnetic position detection systems have proven their worth, particularly due to the easy integration of the electromagnetic locators in medical instruments and due to their high reliability. Electromagnetic position detection systems have a field generator which, for example, is embodied as a head cushion for the patient or which is arranged next to the patient. The field generator emits an alternating electromagnetic field. The locators of an electromagnetic position detection system have coils which are connected to an evaluation unit of the position detection system. An electric current is induced in each coil depending on the alignment and location of the coils in the alternating electromagnetic field. The evaluation unit can determine the exact position of the locator relative to the field generator on account of the level of current. Since the position of the field generator is known in the reference coordinate system, the position of the respective locator is therefore known in the reference coordinate system.

So that the position of the work point of an instrument tip is also determinable in the reference coordinate system, the corresponding instrument must initially be registered or calibrated in the position detection system. To this end, a reference point known in the reference coordinate system, e.g. a point on the patient locator, is driven at by the work point of the medical instrument. The position detection system can determine the direction vector of the distance of the work point relative to the locator of the instrument by way of the position of the locator of the instrument and the position of the reference point in the reference coordinate system of the position detection system. By means of an instrument database, an image, true to its position, of the corresponding instrument can be generated on the display unit by the position detection system.

Moreover, the patient also needs to be registered in the position detection system. To this end, the patient locator is initially attached to the patient. Reference points on the body of the patient are driven to by means of a pointer, the sensing tip of which is registered in the position detection system. Body parts which have little tissue between the skin and bones, such as e.g. joints, are particularly suitable as reference points. As result of this, the accuracy of the registration process of the patient is improved. When a reference point is reached, reaching the respective point can be confirmed manually such that the position detection system can establish the coordinates of the reference point by way of the position data of the pointer and subsequently store these. In some systems, brief dwelling at the reference point is sufficient for initiating an automatic establishment and storage process for the coordinates of the reference point. The more reference points are driven to, the more exactly the position detection system is able to transfer image data of the patient, obtained preoperatively and/or intraoperatively, into the reference coordinate system.

Medical instruments are either reusable instruments, so-called "multiple-use" instruments, which are to be sterilized prior to and after each use in order to reduce the infection risk for the patient, or disposable instruments, so-called "single-use" instruments, which are generally packaged in a sterile fashion and which must be disposed of after use.

Conventional position detection systems are disadvantageous in that the use of medical instruments which have a relatively flexible region between the work point and the locator thereof leads to incorrect determinations of the work point if the work point is deflected from the natural position thereof relative to the locator of the medical instrument as a result of a resistance, e.g. the tissue of the patient. In the process, the flexible instrument shaft is usually deformed elastically. When the resistance drops, the work point springs back into its original position relative to the locator. The conventional position detection systems are not able to compensate the bending of the shaft part between the locator and the work point and therefore establish coordinates of a (fictitious) work point in the case of an unbent instrument shaft. In order to keep such incorrect determinations as small as possible, the locator is arranged as closely as possible to the work point of the instrument tip in the case of medical instruments with a flexible shaft. A minimum distance between the work point and the locator is predetermined, for example by the size of the locator. Therefore, conventional position detection systems are not able to accurately determine the position of the work point of the medical instrument in the case of an unbent instrument shaft.

Conventional multiple-use instruments are disadvantageous in that the work point must be registered in the position detection system prior to each use, as the instrument may be plastically deformed. An additional problem in the case of single-use instruments is that the locators which are arranged in the single-use instrument are comparatively expensive and generally need to be disposed of together with the single-use instrument. This regularly creates high additional costs.

SUMMARY OF THE INVENTION

Therefore, it is the object of the present invention to provide a surgical instrument with a locator arrangement, by means of which the position of the work point is determinable significantly more accurately when the shaft is bent than in the case of conventional position detection systems. Furthermore, the surgical instrument should be usable in the position detection system without an additional registration process, but nevertheless enable a reliable determination of the location of the work point by the position detection system. Finally, a single-use embodiment of the medical instrument should cause fewer additional costs than a conventional single-use instrument.

According to the invention, the object is achieved by a surgical instrument comprising an instrument handle, an instrument shaft connected to the instrument handle, an instrument tip which is connected to the instrument shaft and which has a work point, and a first locator arranged at the instrument handle or the instrument shaft. The shaft is deflectable between the first locator and the work point during use of the surgical instrument, for example due to a force exerted on the work point of the instrument. A second locator is arranged at a distance from the first locator and, compared with the latter, closer to the work point of the surgical instrument. The second locator is embodied to detect fewer than six, but rather e.g. only five degrees of freedom. In this way, the second locator has smaller dimensions than a locator of substantially identical construction which is embodied to detect six degrees of freedom. Furthermore, the second locator is more cost-effective than the first locator of identical construction, as it requires fewer components. Since surgical instruments generally taper from the instrument handle toward the instrument tip and due the smaller dimensions of the second locator, the second locator is arrangeable closer to the work point on the surgical instrument than a locator with larger dimensions. Therefore, it is possible to establish bending of the surgical instrument between the first locator and the second locator and take this into account when determining the position of the work point. To this end, it is also possible to use a bending characteristic of the instrument such that the bending of the instrument between the second locator and the work point can be established at least by calculation. The accuracy of the determination of the work point is therefore significantly improved over conventional position detection systems. With the aid of the first locator, the degree of freedom not detected by the second locator can also be determined on the basis of known geometric data.

Preferably, the work point is the distal end of the instrument tip.

In an advantageous refinement of the invention, the first locator is embodied to detect six degrees of freedom. Therefore, the position of the surgical instrument is determinable by the position detection unit purely on the basis of the data established by way of the first position sensor. The first locator supplies the position of the instrument to the position detection system, while the second locator provides information in respect of determining the deformation of the instrument to the position detection system.

Particularly preferably, the second locator has smaller dimensions than the first locator. Since, for example, there is sufficient space for the first locator in the instrument handle and the surgical instrument tapers from the instrument handle to the work point, the first locator can have larger dimensions than the second locator. The smaller the second locator is, the closer it is arrangeable to the work point.

More preferably, the second locator has a diameter of less than 0.5 mm, in particular less than 0.4 mm. Hence, the second locator is arrangeable in the vicinity of the work point, even in the case of strongly tapering instruments or at relatively small diameters.

Preferably, the second locator is embodied as a position sensor and it has a coil. Position sensors are used in electromagnetic position detection systems. If such a position sensor is arranged in an alternating electromagnetic field, a current is induced in the position sensor, in the coils of the position sensor, in a manner dependent on the position—i.e. the location and orientation—of the position sensor. On account of the known arrangement of the coils and the strengths of the currents induced in the coils, the position detection system can determine the position of the position sensor within the electromagnetic field. Five degrees of freedom are determinable by means of one coil. As result of this feature, the second locator can have a single coil and, in the case of a corresponding design, it can be arranged in the interior of the surgical instrument and hence it is protected from external influences. This is particularly advantageous if the surgical instrument should be easily sterilizable.

Particularly preferably, the first locator is embodied as a position sensor and has two coils. This has the same advantages as in the case of the second position sensor. In the case where the first and second locators are embodied as a position sensor, a purely electromagnetic position detection system is sufficient for determining the position of the surgical instrument and the location of the work point in the reference coordinate system.

Alternatively or additionally, the first locator has at least one reflector for light waves and/or sound waves. Hence, the position of the surgical instrument is determinable by way of optical and/or acoustic means. By way of example, such surgical instruments are employable in position detection systems which do not have a field generator for emitting an alternating electromagnetic field. Accordingly, an electromagnetic position detection system is only still required for the second locator; it can, for example, have a very compact embodiment and easily be integrated into an existing optical and/or acoustic position detection system.

Preferably, the instrument shaft has greater flexibility than the instrument tip. Since the surgical instrument is generally manufactured from one material, different degrees of flexibility are obtainable by way of different second moments of area. Greater flexibility is accordingly obtained, for example, by reducing the cross section. A further measure for increasing the flexibility lies in changing the form of the cross section, and so the instrument has different, direction-dependent flexibilities in such a portion.

Likewise preferably, the instrument shaft has greater flexibility than the instrument tip. This substantially restricts the deformation of the surgical instrument to the instrument shaft, while the instrument tip is subject to lower or negligible deformation. Therefore, if the deformation of the instrument shaft, which is easily establishable by way of the first and second locators, is known, the location of the work point of the instrument is easily determinable.

More preferably, the instrument tip has less flexibility between the second locator and the work point than in the remaining part of the instrument tip. As result of this, the location of the work point is determinable more accurately since all instances of deformation or bending of the instrument, which occur between the locators, are establishable by way of the two locators and possible bending of the region of the instrument tip arranged between the second locator and the work point is negligibly small due to the lower flexibility. In this case, it is also advantageous if the second locator is arranged as close as possible to the work point in order to further increase the accuracy of the determination of the work point.

Advantageously, the surgical instrument is a sickle knife or antrum spoon.

In an advantageous refinement of the invention, the surgical instrument has a memory unit for storing relative location data of the second locator relative to the first locator and/or for storing relative location data of the work point relative to the second locator and/or for storing relative location data of the work point relative to the first locator. As a result, possible deformations of the instrument, which were established in a registration process, can be stored in the instrument. In the case of a new registration of the instrument, these data are retrievable by the position detection system and a new registration is not required. Furthermore, it is therefore also possible in the case of unused instruments for the relative location of the work point in relation to the first locator and/or the second locator to have been stored prior to delivery such that registration of the instrument in the position detection system is not required—to the extent that the work point of the instrument was not displaced by a plastic deformation.

Particularly preferably, the second locator is arranged within an external contour of the surgical instrument. Hence, the second locator is better protected from external influences. This is advantageous, in particular, because the surgical instrument must be easily sterilizable. Furthermore, the instrument is more easily sterilizable if the surface has less unevenness.

In a preferred embodiment of the invention, the second locator is arranged in the surgical instrument at a distance of less than 2 cm from the work point. Particularly preferably, the second locator is arranged in the instrument at a distance of less than 1 cm from the work point. The closer the locator is arranged at the work point, the more accurately the position of the work point is determinable by the position detection system since possible bending of the instrument is measurable over a larger part of the instrument and therefore more precisely establishable.

Preferably, the first locator and the second locator are arranged at the surgical instrument in such a way that the position detection system identifies the type of employed surgical instrument on the basis of characteristic values, provided to the position detection system, relating to surgical instruments and the respective arrangement of the locators at the surgical instrument. Accordingly, it is preferable for each surgical instrument used in a position detection system to have an individual arrangement—relative position—of the locators with respect to one another. During the registration of the surgical instrument in the position detection system, in the case of which the surgical instrument is not deformed by pressure forces, the system automatically identifies the position of the first locator and second locator and it can therefore determine the relative position of the locators from one another. By matching the relative positions of the locators to a database, in which surgical instruments with the respective relative positions of the locators are stored, the position detection system is able to determine the surgical instrument and the relevant characteristics, such as e.g. the name, the dimensions of the instrument or the position of the work point in relation to the first and/or second locator. Therefore, calibrating the work point in the position detection system is only still required in cases where the instrument has been plastically deformed.

More preferably, the instrument tip with the instrument shaft is detachably arrangeable at the instrument handle, wherein the first locator is arranged in the instrument handle and the second locator is arranged in the instrument shaft or the instrument tip. Alternatively or additionally, them instrument tip can be detachably arranged on the instrument shaft. In this alternative embodiment, the second locator is arranged in the instrument tip and the first locator is arranged in the instrument handle or the instrument shaft. After assembling the instrument handle, instrument shaft and instrument tip, the first locator and the second locator, and hence the work point of the surgical instrument, are detectable by the position detection system. Hence, the instrument is automatically calibratable. Furthermore, in the case of a single-use instrument, only the part of the surgical instrument which the more cost-effective second locator must be disposed of after use In this case, the second locator can be arranged e.g. concentrically about the lumen in the form of a hollow coil, either within or outside of the lumen. More preferably, the instrument shaft and the instrument handle likewise have a continuous lumen, which forms a continuous lumen with the lumen of the instrument tip when the instrument handle, instrument shaft and instrument tip are assembled. At the proximal end, the instrument handle has an opening for the lumen. By way of example, the opening can be embodied as a connector for a tube.

Preferably, the instrument tip is connectable to the instrument shaft and the instrument shaft is connectable to the instrument handle by way of clamping connection or Luer lock connection. By way of example, a clamping connection can comprise a recess in the instrument shaft or instrument handle, into which the instrument tip or instrument shaft, respectively, is insertable and affixable in said recess by means of a clamping screw. In the case of a Luer lock connection, it is advantageous if the instrument tip or the instrument shaft has the male part and the instrument shaft or the instrument handle has the female part of the Luer lock connection. By way of such connections, the instrument handle, instrument shaft and instrument tip are held against one another in a secure and re-detachable manner such that an unwanted relative movement between the instrument handle, instrument shaft and instrument tip, which are connected to one another, is prevented. However, according to the invention, it is also possible to provide a plug-in and/or screw connection with virtually any design.

Advantageously, the instrument handle, instrument shaft instrument tip have electrical connections, by means of which an electrical connection between the instrument parts is establishable when the instrument handle, instrument shaft and instrument tip are coupled. Such an electrical connection can be configured for transferring electrical signals and for providing an electrical voltage. Preferably, the electrical connection comprises a plug and a fitting socket, with the poles of the electrical connection preferably being arranged coaxially. In an advantageous refinement of the invention, the electrical connection comprises a multi-pole jack plug, which is arrangeable coaxially with the instrument axis, and a fitting jack socket. According to the invention, the electrical connection can also comprise electrically conductive contact plates, against which electrically conductive contact elements can be pressed under the application of a spring force. By way of example, the contact elements can comprise bent plate strips, which can generate a spring force due to the form thereof. Alternatively, the contact elements can comprise spheres which are pressed in the direction of the corresponding contact plate, for example by means of a coil spring.

Preferably, the instrument tip and/or the instrument shaft have an identification apparatus, which provides information about the instrument tip. More preferably, the identification apparatus is embodied to provide the information about the identity of the instrument tip to a control unit of the medical instrument. The control unit is preferably arranged outside of the surgical instrument, for example in a housing that is separate from the surgical instrument. The control unit is coupleable to the surgical instrument by means of signal transfer means, such as e.g. cables or radio waves.

The identification apparatus can comprise information about the properties of the instrument tip. This can include, for example, the position and alignment of the work point of the instrument tip, in particular relative to the region of the instrument tip which engages with the instrument shaft during operation, form, material, hardness and flexibility and/or mechanical resilience of the instrument tip. Alternatively, these data or some of these data can be stored in a memory unit coupled to the control unit such that the control unit can read out the data associated with the respective instrument tip from the memory unit after the identification of an instrument tip placed onto the instrument shaft. Furthermore, the identification apparatus preferably comprises corresponding information about the instrument shaft.

Preferably, the identification apparatus has information about the type, design and/or model name of the instrument tip. Such information serves the control unit for the exact identification of the employed instrument tip. This information is comparable with stored information about the instrument tip, and so e.g. position and alignment of the work point of the instrument tip, in particular relative to the region of the instrument tip which possibly engages with the instrument shaft, form, material, hardness and flexibility and/or mechanical resilience of the instrument tip are establishable on the basis of this information. Likewise, the information can be used to control specific properties of the software (e.g. visualization of the navigation point, visualization of the geometry of the instrument, which slice images are displayed, optionally superimpose target view, select filters for the signal data processing). Furthermore, the identification apparatus preferably comprises corresponding information about the instrument shaft.

In accordance with a preferred embodiment, the information from the identification apparatus is transferable to the control unit by way of the instrument shaft. To this end, the instrument shaft or the instrument handle can have readout means such as e.g. a scanner or surface scanner. Furthermore, an electrical connection may be provided between the instrument tip and the instrument shaft for the purposes of transferring the information. Alternatively, the readout means can be arranged in a readout unit which is arranged outside of the medical instrument and which is to be connected to the control unit, e.g. by means of a cable for data transfer or wirelessly by way of a radio connection.

Preferably, the identification apparatus has an electronic memory, a graphically depicted code, a magnetic code and/or a plug-in connection. The corresponding information is stored in the form of electrical signals in the electronic memory, such as e.g. a ROM or EPROM, and it can be read out in a known manner. A graphically depicted code could be e.g. a barcode, which can be read by way of a laser scanner. Furthermore, information can be stored on magnetized regions in the form of a magnetic code. By way of example, bridge connections can be considered as plug-in connections, in which a specific code is representable by the connection of corresponding contacts or pins by means of suitable electrically conductive bridges.

In a preferred embodiment of the invention, the instrument tip and the instrument shaft have at least one continuous lumen, for example destined as a rinse/suction tubule.

In an alternative embodiment of the invention, the second locator or the first locator is arranged in a drill sleeve. The drill sleeve is arrangeable on the patient and the surgical instrument is insertable into the drill sleeve in accordance with its intended purpose. Therefore, the position of the drill sleeve is determinable relative to the patient. Since the surgical instrument is insertable into the drill sleeve, the position of the work point of the instrument can be established by way of the insertion depth of the instrument into the drill sleeve This is possible since the instrument is only displaceable along a trajectory relative to the drill sleeve. Therefore, the depth can be established by way of e.g. measurement markers on the surgical instrument. Alternatively, the surgical instrument likewise can have a locator for determining the depth and the work point. The position of the surgical instrument relative to the patient is establishable by determining the position of the drill sleeve relative to the patient and the position of the surgical instrument relative to the drill sleeve. This embodiment is advantageous in that it is also possible to determine the work point of a surgical instrument which is not attached to a position detection system by way of the position of the drill sleeve relative to the patient and the position of the surgical instrument relative to the drill sleeve.

Furthermore, the object of the invention is achieved by a position detection system for establishing the position of surgical instruments, comprising an evaluation unit for establishing the position of locators arranged in the position detection system and a display unit for displaying the surgical instrument in its true position, wherein the surgical instrument has a locator arrangement according to the invention.

The object of the invention is likewise achieved by a method for detecting the position of a surgical instrument, wherein the instrument has an instrument handle, an instrument shaft which is connected to the instrument handle and which is deflectable during use of the surgical instrument, an instrument tip which is connected to the instrument shaft and which has a work point, and wherein a first locator is assigned to the instrument in a manner that is spatially defined at at least one instant and a second locator is arranged at the instrument in the vicinity of the instrument tip, wherein the second locator is embodied to detect five degrees of freedom, wherein the method comprises the following steps:

determining an instrument-specific calibration vector from the second locator to the work point in the coordinate system of the first locator in the case of a non-deflected instrument shaft, wherein the determination is preferably carried out initially;

determining the location and direction of the work point in the reference coordinate system by transforming a current coordinate of the second locator, displaced by the calibration vector, into the coordinate system of the first locator, wherein the transformation is preferably carried out in each measurement cycle.

Preferably, provision is made for the second locator to supply a location and for the first locator to supply a direction for the transformation of the work point.

In a preferred refinement of the method, the first locator is arranged at the instrument handle or the instrument shaft and the instrument shaft is deflectable between the first locator and the work point during use of the surgical instrument. The second locator can be arranged at a distance from the first locator and, compared with the latter, closer to the work point.

In a particularly preferred refinement, the work point lies away from an instrument axis.

The first locator can be a patient locator, which is arranged separately from the instrument and securely on the patient. The first locator can be a drill sleeve, which is arranged separately from the instrument and securely on the patient. Preferably, the instrument is insertable into the drill sleeve and the method comprises the following step:

establishing the location of the work point of the instrument by way of an insertion depth of the instrument into the drill sleeve.

It was found to be advantageous if the method comprises storing the calibration vector in a memory, in particular in an instrument memory, and determining the location and alignment of the work point in the reference coordinate system after reading out the calibration vector from the memory.

The invention includes the discovery that surgical instruments are equipped with thin shafts (antrum spoon, sickle knife, etc.) for minimally invasive access or accesses through natural body orifices (e.g. nose). In these instruments, the work point (instrument tip) can lie away from the axis of the shaft, as a result of which an elastic deformation of the shaft as a result of the applied forces is to be expected when working with the instrument.

In order to navigate such surgical instruments with a thin shaft, a locator can be integrated into the shaft, preferably directly at the end of the work point. As a result, the deformation of the shaft is negligible for the detection of the location of the work point.

The invention likewise includes the discovery that the locator can be embodied with a small diameter (<0.5 mm, in particular <0.4 mm), if one degree of freedom is dispensed with (5DOF sensor).

Errors in the orientation information (in the 6DOF sensor) have a smaller effect than in instruments with sensors only in or on the handle, as the distance between the 5DOF sensor and navigated instrument work point is small.

In order to calibrate an instrument work point away from the coil or shaft axis, a second and third coil sensor can be integrated in the instrument (e.g. in the handle). Together, these sensors form a locator with 6 degrees of freedom (6DOF sensor).

Furthermore, the invention comprises a method for calibrating a first locator of an instrument shaft to a work point of an instrument tip, arrangeable on the instrument shaft in a work position, in a position detection system with a control unit, wherein the instrument tip has a second locator which is calibrated to the work point of the instrument tip. The method is characterized by the following steps:

arranging the instrument tip on the instrument shaft in the work location, registering the instrument tip at the control unit, establishing the geometry of the instrument tip and the position of the second locator in relation to the first locator and the work point on the basis of the information about the instrument tip collected during the registration of the instrument tip, detecting the position of the work point of the instrument tip within the position detection system due to the sensor signal of the second locator and the established information about the geometry of the instrument tip, detecting the sensor signal of the first locator, calibrating the second locator to the work point of the instrument tip using the sensor signals of the second locator and the first locator and the information about the position of the work point relative to the second locator.

The instrument tip can be registered to the control unit before or after or during the arranging of the instrument tip at the instrument shaft in the work position. The data about the geometry of the instrument tip and/or the position of the second locator in relation to the work point of the instrument tip can be stored either in a memory unit in the instrument tip or in a database arranged outside of the instrument tip. In the latter case, it is sufficient for the instrument tip merely to be identified when registering the instrument tip to the control unit and for the control unit to read out the corresponding data of the respective instrument tip from a memory unit.

The first locator can be a proximal sensor of an instrument shaft. The second locator can be a distal sensor of an instrument tip.

BRIEF DESCRIPTION OF THE DRAWINGS

Below, the invention is intended to be explained in more detail on the basis of an exemplary embodiment, with reference being made to the figures. In detail.

DETAILED DESCRIPTION

Figure 1:
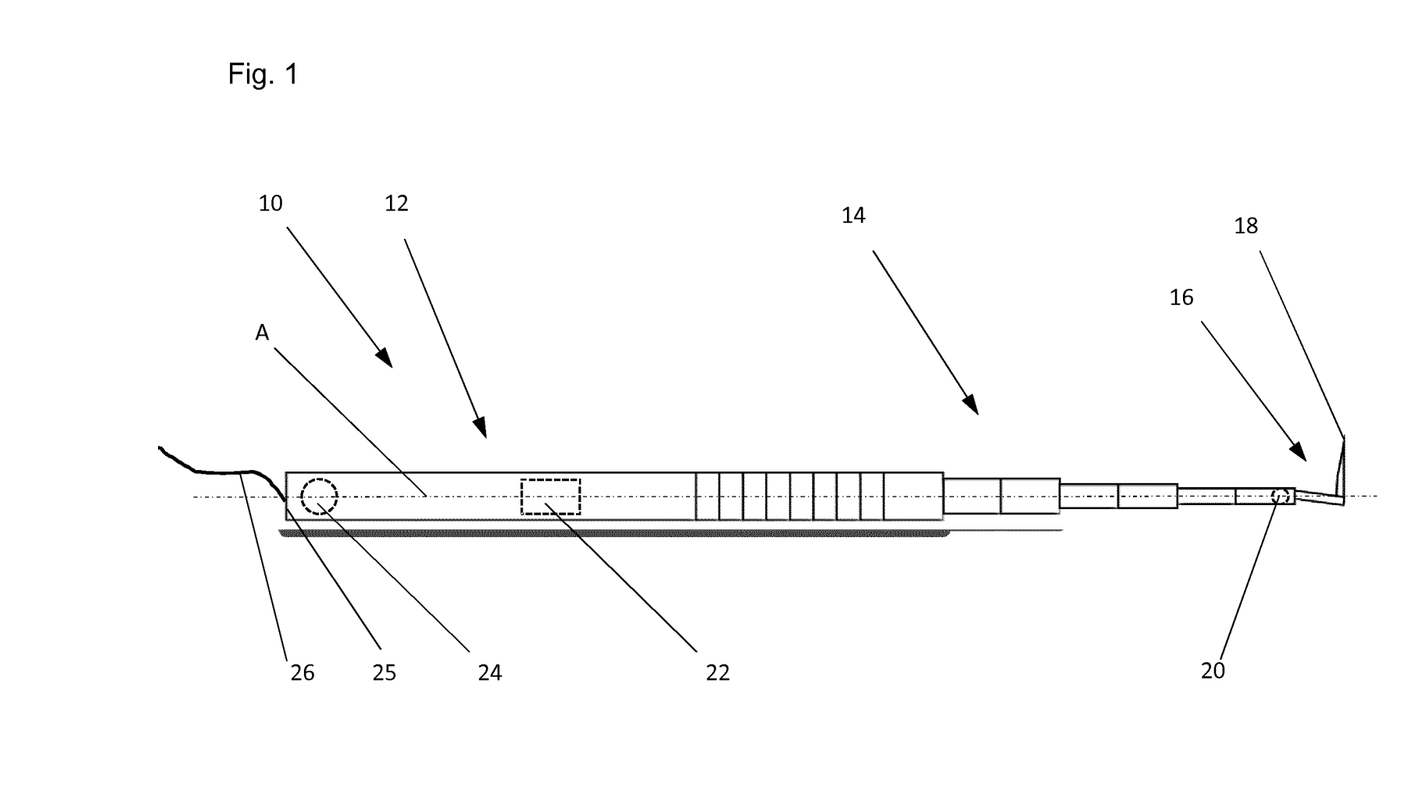
FIG. 1 shows a schematic side view of an integral embodiment of a surgical instrument according to the invention.

The surgical instrument 10 shown in FIG. 1 has an instrument axis A, an elongate, substantially cylindrical instrument handle 12, an elongate, cylindrical instrument shaft 14 in the form of a stepped cone and arranged coaxially at the distal end of the instrument handle 12 and an angled instrument tip 16 arranged at a distal end of the instrument shaft 14. Instead of the cylindrical form, the surgical instrument 10 can also be embodied in a substantially cuboid manner or have an oval cross section. At the distal end, the instrument tip 16 has a work point 18 which is not arranged on the instrument axis A in this embodiment. In alternative embodiments, the work point 18 can also be arranged on the instrument axis A.

The instrument shaft 14 has a smaller diameter than the instrument handle 12 and the instrument tip 16 has a smaller diameter than the instrument shaft 14. In this embodiment, the instrument shaft 14 is many times longer than the instrument tip. A force component acting perpendicularly to the instrument axis on the work point 18 causes bending of the surgical instrument 10, substantially in the region of the instrument shaft 14.

A second locator 20 is arranged in a region of the instrument shaft 14 adjacent to the instrument tip 16. The second locator 20 is preferably arranged in a cavity of the instrument shaft 14. A locator cable (not identifiable in this illustration) extends, within the interior of the surgical instrument 10 from the second locator 20 to a proximal end 25 of the surgical instrument 10. The second locator 20 is arranged as close as possible to the work point 18 of the instrument tip 16. The locator 20 can also be arranged in the instrument tip 16. The second locator 20 is preferably a position sensor with a single coil for an electromagnetic position detection system.

In an alternative embodiment of the invention (not depicted here), the surgical instrument 10 has a plurality of second locators 20, which are arranged next to one another in the instrument shaft 14 or in the instrument tip 16 along the instrument axis A. This arrangement enables a reduction in the degrees of freedom establishable by the individual second locators 20 and therefore a reduction in the dimensions of the individual second locators 20. Here, it is important that this multiplicity of second locators 20, in the totality thereof, is embodied to establish the same number of degrees of freedom as a single second locator 20.

In the preferred embodiment of the invention shown in FIG. 1, a first locator 24 is arranged in the instrument handle 12 in the vicinity of the proximal end 25. The first locator 24 is preferably arranged in a cavity of the instrument handle 12. A locator cable (not depicted here) leads from the first locator 24 to the proximal end 25 of the surgical instrument 10 and preferably extends within the interior of the instrument handle 12. In an alternative embodiment, the first locator 24 is arranged in a different region of the instrument handle 12 or in the instrument shaft 14, wherein the first locator 24 is arranged closer to the proximal end 25 of the surgical instrument 10 than the second locator 20. The first locator 24 is preferably a position sensor with two coils for use in an electromagnetic position detection system such that the first locator 24 can detect all six degrees of freedom.

In an alternative embodiment (not depicted here), the surgical instrument 10 can have a plurality of first locators 24, which are arranged in the instrument handle 12 and/or the instrument shaft 14. The first locators 24 are preferably embodied to detect at least six degrees of freedom in the totality thereof. Preferably, the first locators 24 detect redundant signals such that, for example, the defect of a first locator 24 is easily establishable.

In the preferred embodiment of the invention shown in FIG. 1, a memory unit 22 is arranged in the instrument handle 12. A memory cable (not depicted here) is led from the memory unit to the proximal end of the surgical instrument 10 and it preferably extends within the interior of the instrument handle 12. Position data, e.g. relative positions of the work point 18 in relation to the first locator 24 and/or in relation to the second locator 20 and/or of the first locator 24 in relation to the second locator 20 are stored or storable in the memory unit 22. These position data are readable by the position detection system and a surgical instrument 10 is therefore registrable in the position detection system.

Figure 3:
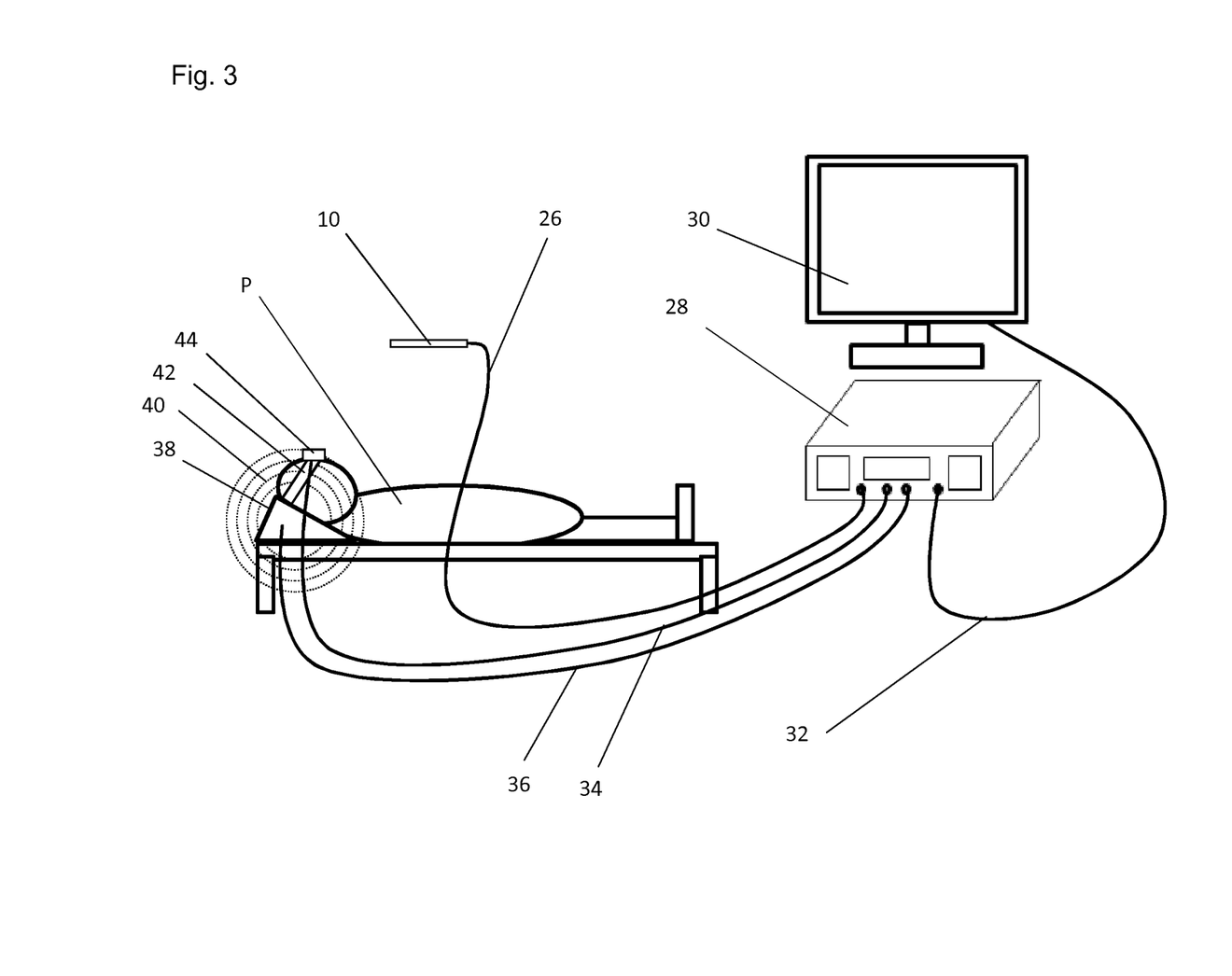
FIG. 3 shows a schematic view of a position detection system according to the invention for establishing the position of surgical instruments.

The locator cable and the memory cable extend in an instrument cable 26 from the proximal end 25 of the surgical instrument 10 to an evaluation unit 28 depicted in FIG. 3.

Figure 2:
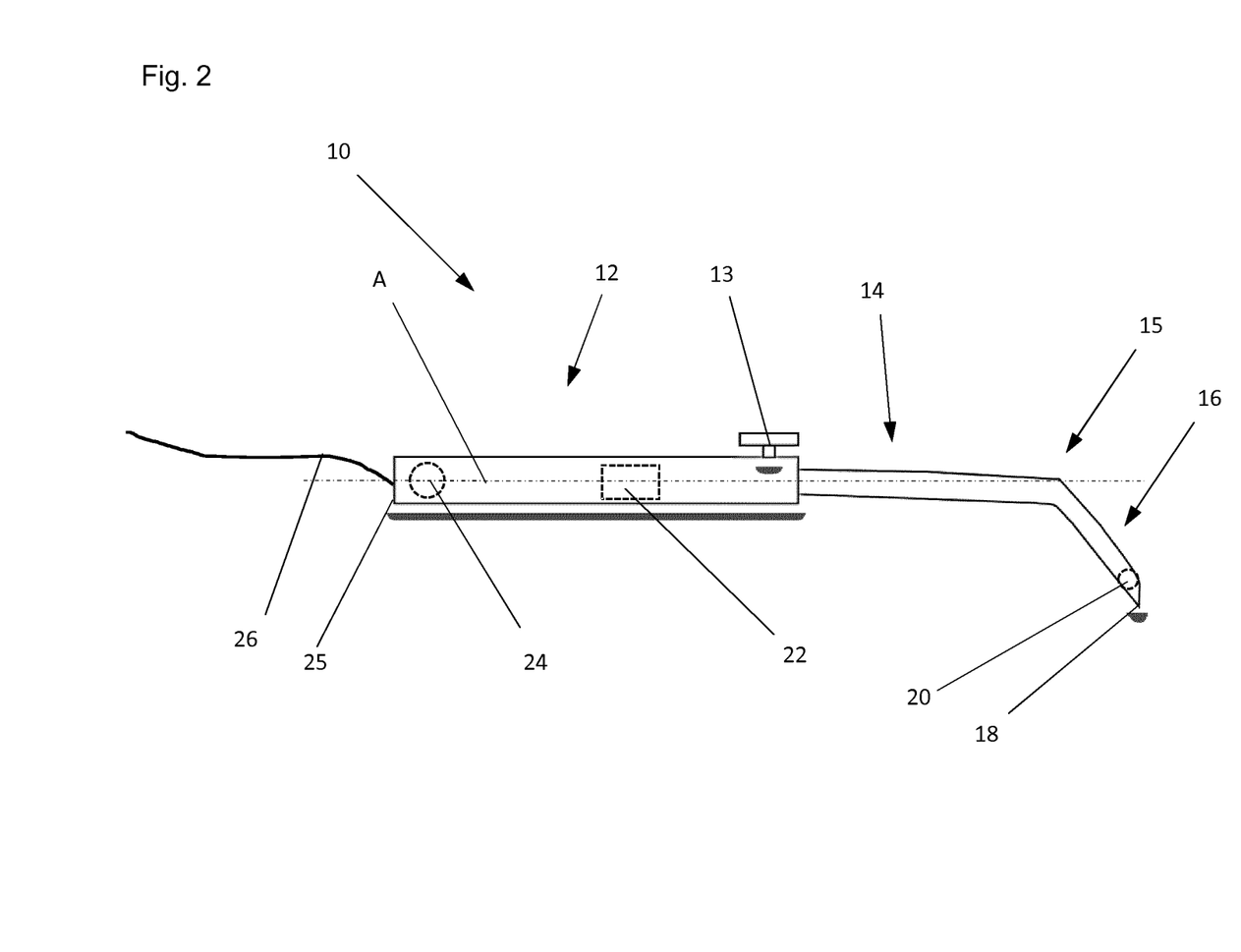
FIG. 2 shows a schematic side view of a two-part embodiment of a surgical instrument according to the invention.

The two-part surgical instrument 10, depicted schematically in FIG. 2, has an instrument handle 12, an instrument shaft 14 and an instrument tip 16 with a work point 18 arranged at a distal end of the instrument tip 16. A second locator 20 is arranged immediately adjacent to the work point 18 in the instrument tip 16. The position of the second locator 20 therefore substantially corresponds to the position of the work point 18. Furthermore, a transition region between the instrument tip 16 and the instrument shaft 14 has an offset embodiment. In alternative embodiments (not depicted here), the instrument shaft 14, instrument tip 16 and, transition region 15 can have virtually any form suitable for a surgical instrument.

In the embodiment depicted in FIG. 2, a first locator 24 is arranged in the instrument handle 12 adjacent to the proximal end 25. Alternatively, the first locator 24 can also be arranged in any other region of the instrument handle 12 or instrument shaft 14.

A proximal end of the instrument shaft 14 is held in the distal end of the instrument handle 12 and fixed in this position by way of a clamping screw 13. In the depicted exemplary embodiment, the regions of the instrument shaft 14 and instrument handle 12 engaging into one another have a round cross-sectional area. Preferably, these portions are flattened or have a polygonal, in particular triangular, square, pentagonal or star-shaped cross section and/or a guideway, e.g. according to the tongue and groove principle, in order to prevent relative twisting of instrument shaft 14 and instrument handle 12 by way of an interlock. Embodiments according to the invention are provided, in which these portions are embodied in such a way that the instrument handle 12 and the instrument shaft 14 can only be brought into engagement in a fixed mutual alignment.

In the assembled state of the surgical instrument 10 depicted in FIG. 2, the instrument handle 12 and instrument shaft 14 are connected to one another both mechanically and electrically by way of electrical contacts not visible in this view. Sensor signals of the second locator 20 can be transferred to the instrument handle 12 by way of this electrical connection. Arranged at the proximal end 25 of the instrument handle 12 is an instrument cable 26 for transferring the locator data from the first locator 24 and from the second locator 20 to an evaluation unit 28 depicted in FIG. 3.

The example of an electromagnetic position detection system depicted in FIG. 3 has a surgical instrument 10 according to the invention, which is connected by way of the instrument cable 26 with the evaluation unit 28. The evaluation unit 28 is connected by way of a display cable 32 to a display unit 30 in order, for example, to depict an image of the surgical instrument 10, true to its position, in a reference coordinate system. Optionally, image data of a patient P, obtained preoperatively and/or intraoperatively, are displayable on the display unit 30 in a superposed manner and/or next to or over one another. Preferably, the display unit 30 is embodied to particularly highlight the work point 18 of the surgical instrument 10 and/or structures of the patient P, which are of particular interest to the surgeon, such as e.g. sensitive structures which may not be damaged, or tissue which needs to be treated or removed, graphically, for example by colored markings or appropriate labels.

The evaluation unit 28 is connected by way of a patient locator cable 34 to a patient locator 44, which is held on the forehead of the patient P by means of a fastening band 42. The patient P is registrable in the position detection system by means of the patient locator 44 in order to establish the position of the patient P in the reference coordinate system. A field generator cable 36 connects the evaluation unit 28 to a field generator 38, which is embodied as a headrest in this example. The field generator 38 emits an alternating electromagnetic field 40, which extends at least over the region of the patient P in which the operation is to be carried out. The position detection system depicted in FIG. 2 is therefore able to accurately determine the location of the work point 18 of the surgical instrument 10, even if the work point 18 of the surgical instrument 10 is deflected from the relative position thereof in relation to the instrument handle 12 or in relation to the first locator 24, for example due to pressure forces exerted on the surgical instrument 10 during the operation.

Figure 4:
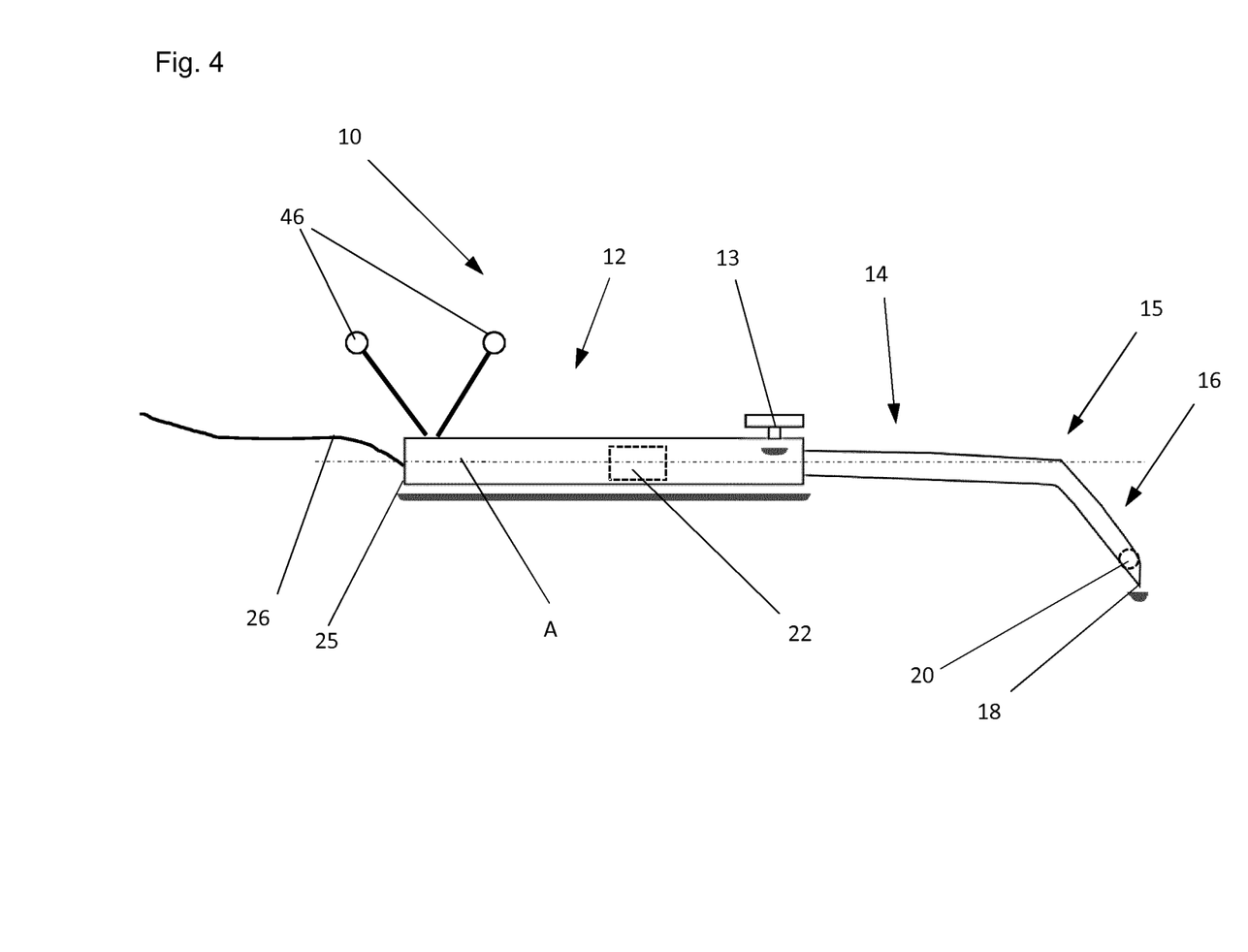
FIG. 4 shows a schematic side view of a surgical instrument according to the invention, comprising optical reflectors as a first locator for optical position detection.

FIG. 4 schematically shows that an optical locator with a plurality of reflectors 46 can also be provided in place of, or in addition to, a first locator 24 in the form of a position sensor with sensor coils.

Figure 5:
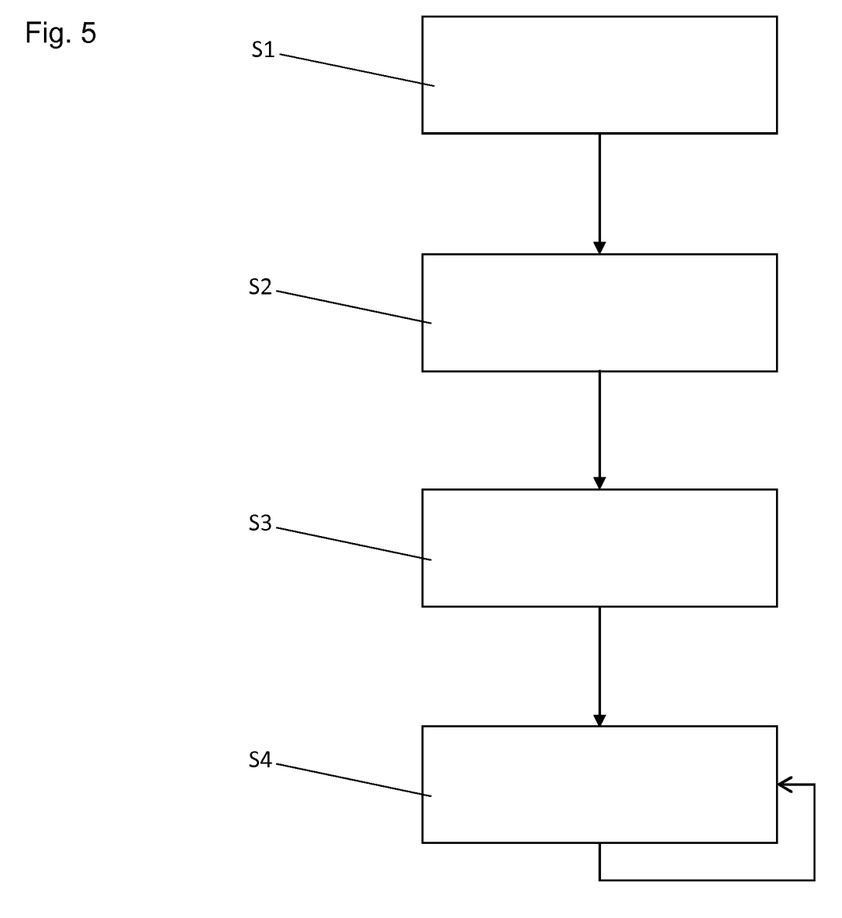
FIG. 5 shows a schematic illustration of a method according to the invention for detecting the position of a surgical instrument.

A schematic illustration of a method according to the invention for detecting the position of a surgical instrument, for example the instrument described with reference to FIG. 1, is shown in FIG. 5.

In a first step S1, an instrument-specific calibration vector from the second locator to the work point is initially determined in the coordinate system of the first locator in the case of a non-deflected instrument shaft.

In a second step S2, the calibration vector is stored in an instrument memory.

In a third step S3, the calibration vector is read from the memory.

In a fourth step S4, the location and direction of the work point is determined in the reference coordinate system by transforming a current coordinate of the second locator, displaced by the calibration vector, into the coordinate system of the first locator.

The transformation is carried out in each measurement cycle.

LIST OF REFERENCE SIGNS

10 Surgical instrument
12 Instrument handle
13 Clamping screw
14 instrument shaft
15 Transition region
16 Instrument tip
18 Work point
20 Second locator
22 Memory unit
24 First locator
25 Proximal end
26 Instrument cable
28 Evaluation unit
30 Display unit
32 Display cable
34 Patient locator cable
36 Field generator cable
38 Field generator
40 Electromagnetic field
42 Fastening band
44 Patient locator
46 Optical reflector
A Instrument axis
P Patient The invetion claimed is:

1. A surgical instrument comprising:
an elongate instrument handle having a proximal end and a distal end;
an elongate straight instrument shaft connected to the distal end of the instrument handle and defining an instrument axis, the instrument shaft having a proximal end and a distal end, the proximal end of the instrument shaft being connected to the instrument handle, the instrument shaft being bendable in response to a force component acting perpendicular to the instrument axis;
a narrow angled instrument tip integrally connected to the distal end of the straight instrument shaft, the angled instrument tip having a work point which is configured to elastically deform away from the instrument axis;
a first locator arranged at the instrument handle, wherein the first locator comprises a position sensor having two coils and configured to detect six degrees of freedom; and
a second locator arranged at the distal end of the straight instrument shaft adjacent to the instrument tip, wherein the second locator comprises a position sensor having one coil, has smaller dimensions than the first locator, and is configured to detect five degrees of freedom, wherein the first locator is arranged closer to the proximal end of the handle than the second locator, and the second locator is arranged at a distance from the first locator closer to the work point, and wherein the instrument shaft is bendable between the first locator and the distal end of the instrument shaft during use of the surgical instrument.

2. The surgical instrument ofclaim 1, wherein the second locator has a diameter of less than 0.5 mm.

3. The surgical instrument of claim 2, wherein the second locator has a diameter of less than 0.4 mm.

4. The surgical instrument of claim 1, wherein the first locator has at least one reflector for light waves or sound waves.

5. The surgical instrument of claim 1, wherein the instrument shaft has greater flexibility than the instrument handle.

6. The surgical instrument of claim 1, wherein the surgical instrument has a memory unit for storing relative location data of the second locator relative to the first locator, for storing relative location data of the work point relative to the second locator, for storing relative location data of the work point relative to the first locator, or a combination thereof.

7. The surgical instrument of claim 1, wherein the second locator is arranged within an external contour of the surgical instrument.

8. The surgical instrument of claim 1, wherein the second locator is arranged in the distal end of the instrument shaft so as to be at a distance of less than 2 cm from the work point.

9. The surgical instrument of claim 1, wherein the first locator and the second locator are arranged at the surgical instrument such that a position detection system is configured to identify the type of employed surgical instrument on the basis of characteristic values relating to surgical instruments and the respective arrangement of the first locator and the second locator at the surgical instrument.

10. A position detection system for establishing the position of one or more surgical instruments, comprising:
the surgical instrument of claim 1;
an electromagnetic field generator correlated to a reference coordinate system;
an evaluation unit for establishing the position of locators arranged in the position detection system, wherein the evaluation unit is configured to determine an instrument-specific calibration vector from the second locator to the work point in a coordinate system of the first locator where the instrument shaft is straight relative to the instrument axis, and wherein the evaluation unit is further configured to determine a location and direction of the work point in the reference coordinate system by transforming a coordinate of the second locator in the reference coordinate system, displaced by the calibration vector, into the coordinate system of the first locator; and
a display unit for displaying at least one of the one or more surgical instruments in its true position.

11. The position detection system of claim 10, wherein the determination of the calibration vector is performed prior to elastic deformation of the instrument shaft, and wherein the transformation for determination of the location and direction of the work point is performed at each measurement cycle.

12. The position detection system of claim 10, wherein the second locator supplies a location and the first locator supplies a direction for the transformation of the work point.

13. The position detection system of claim 10, wherein the evaluation unit is further configured to store the calibration vector in an instrument memory unit, and to determine the location and alignment of the work point in the reference coordinate system after reading out the calibration vector from the instrument memory unit.

14. The position detection system of claim 10, wherein the position detection system is configured to identify the type of surgical instrument on the basis of characteristic values relating to surgical instruments and the respective arrangement of the first locator and the second locator on the one or more surgical instruments.

15. The surgical instrument of claim 1, wherein the elongate instrument handle is cylindrical, the elongate straight instrument shaft is in the form of a stepped cone, and the angled instrument tip is smaller than the distal end of the instrument shaft.

16. The surgical instrument of claim 1, wherein the part of the angled instrument tip between the second locator and the work point is less flexible than the remaining part of the angled instrument tip.

17. The surgical instrument of claim 1, wherein the instrument shaft is detachably connected to the distal end of the instrument handle.

* * * * *